United States Patent [19]

Che

[11] Patent Number: 4,590,298
[45] Date of Patent: May 20, 1986

[54] PRODUCTION OF HYDROXYKETONES FROM FORMALDEHYDE

[75] Inventor: Tessie M. Che, Westfield, N.J.

[73] Assignee: Celanese Corporation, New York, N.Y.

[21] Appl. No.: 708,619

[22] Filed: Mar. 5, 1985

[51] Int. Cl.$^4$ .............................................. C07C 45/50
[52] U.S. Cl. .................................. 568/387; 568/462; 568/679; 568/863; 518/714; 518/701
[58] Field of Search ............... 568/387, 462, 311, 342; 518/714, 701

[56] References Cited

U.S. PATENT DOCUMENTS

| | | | |
|---|---|---|---|
| 4,096,164 | 6/1978 | Ellgan et al. | 518/714 |
| 4,210,597 | 7/1980 | Huang | 518/714 |
| 4,390,734 | 6/1983 | Knifton | 568/387 |
| 4,405,814 | 9/1983 | Carroll et al. | 568/462 |
| 4,405,821 | 9/1983 | Goety | 568/462 |
| 4,487,972 | 12/1984 | Hoag et al. | 568/387 |

FOREIGN PATENT DOCUMENTS

| | | | |
|---|---|---|---|
| 59-55849 | 3/1984 | Japan | 568/387 |
| 59-108735 | 6/1984 | Japan | 568/387 |

Primary Examiner—James H. Reamer
Attorney, Agent, or Firm—Depaoli & O'Brien

[57] ABSTRACT

This invention provides a process for the production of $C_4$–$C_5$ hydroxyketones by reaction of formaldehyde and synthesis gas in a basic organic solvent in the presence of a tungsten and Group VIII metal-containing catalyst composition.

17 Claims, No Drawings

PRODUCTION OF HYDROXYKETONES FROM FORMALDEHYDE

BACKGROUND OF THE INVENTION

The production of $C_1$–$C_4$ and higher oxygenated hydrocarbons from synthesis gas is described in U.S. Pat. Nos. such as 3,944,588; 3,948,965; 4,115,428; 4,151,192; 4,302,547; 4,315,994; 4,327,190; and references cited therein.

Other prior art of interest relates to the reaction of formaldehyde or methanol with synthesis gas to produce oxygenated hydrocarbons, such as ethylene glycol, acetaldehyde, methyl acetate, butanal and the like, with different catalyst systems.

U.S. Pat. No. 2,451,333 describes a process for reacting formaldehyde and carbon monoxide/hydrogen in contact with a reduced cobalt oxide catalyst to produce organic polyhydroxy compounds such as ethylene glycol and glycerol.

U.S. Pat. No. 4,201,868 describes a process for reacting methanol and carbon monoxide/hydrogen in the presence of cobalt carbonyl associated with an organic nitrogen ligand to produce methyl acetate, acetaldehyde and dimethyl acetal.

U.S. Pat. No. 4,291,179 describes a process which involves reacting formaldehyde and carbon monoxide/hydrogen in the presence of a halogen-containing rhodium catalyst to produce acetaldehyde and ethanol.

U.S. Pat. No. 4,339,608 describes a process which involves the reaction of methanol and carbon monoxide/hydrogen in the presence of a tertiary organo Group VA compound-containing catalyst to produce n-butanol and n-butanal.

U.S. Pat. No. 4,405,814 describes a process for reacting formaldehyde and carbon monoxide/hydrogen in the presence of a rhodium-containing catalyst complex with organophosphine and basic organic amine ligands to produce glycol aldehyde.

There is continuing interest in the development of new and improved catalysts and processes for converting single carbon compounds to higher oxygenated hydrocarbon derivatives.

Accordingly, it is an object of this invention to provide a process for reacting formaldehyde and carbon monoxide/hydrogen to form higher oxygenated hydrocarbons.

It is another object of this invention to provide a process for converting formaldehyde to $C_4$–$C_5$ hydroxyketone products.

It is a further object of this invention to provide a process for producing 3-hydroxy-2-butanone and 4-hydroxy-2-pentanone.

Other objects and advantages of the present invention shall become apparent from the accompanying description and examples.

DESCRIPTION OF THE INVENTION

One or more objects of the present invention are accomplished by the provision of a process for the conversion of formaldehyde to higher oxygenated hydrocarbons which comprises reacting formaldehyde, carbon monoxide and hydrogen in a basic organic solvent medium in the presence of a catalyst composition containing tungsten and Group VIII metal components, to yield a product mixture comprising $C_4$–$C_5$ hydroxyketones.

In another embodiment, this invention provides a process for the production of hydroxyketones which comprises reacting formaldehyde, carbon monoxide and hydrogen in an aprotic organic amide solvent medium in the presence of a soluble catalyst composition containing tungsten and Group VIII 'metal compounds, at a temperature between about 100°–200° C. and a pressure between about 2000–10,000 psi to yield a product mixture comprising 3-hydroxy-2-butanone and 4-hydroxy-2-pentanone.

The term "basic organic solvent" refers to a liquid organic medium which is at least weakly alkaline in reactivity relative to a strong acid. Illustrative of basic organic solvents are amines and amides which have the following base strengths in terms of pKa relative to ammonia (pKa=33), e.g., pyrrolidine (11.3), ethylamine (10.8), diethylamine (11.1), triethylamine (10.8), benzylamine (9.5), morpholine (8.3), pyridine (5.2), aniline (4.6), N-methylacetamide(−0.46), acetamide (−0.63), 2-pyrrolidinone (−0.65), 1-methyl-2-pyrrolidinone (−0.75) and benzamide (−1.5).

The process can be conducted by charging a reactor with solvent medium, formaldehyde and catalyst, and pressuring the reaction system with synthesis gas.

The formaldehyde can be introduced in the form of paraformaldehyde, methylal, formalin solution or polyoxymethylene.

The carbon monoxide/hydrogen gas mixture can be employed in a molar ratio between about 1:10–10:1 of carbon monoxide to hydrogen, with the preferred molar ratio being between about 1:2–2:1 of carbon monoxide to hydrogen. An inert diluent gas such as nitrogen can be included in the pressure system.

The basic organic solvent is employed in a sufficient quantity to provide a liquid phase reaction medium in the reactor. A typical voume of basic organic solvent will range between about 5–100 milliliters per gram of formaldehyde in the reaction medium.

The catalyst composition can be employed in a quantity between about 0.001–1.0 gram-atom of tungsten and Group VIII metals per liter of reaction medium. Typically between about 0.005–0.1 gram-atom of active metal content in the catalyst composition is utilized per liter of reaction medium. With reference to the formaldehyde starting material, the catalyst composition usually is employed in a quantity between about 0.5–20 weight percent, based on the weight of formaldehyde.

The invention process is conducted at a temperature between about 75°–250° C., and usually will be in the range between about 100°–200° C.

The pressure employed in the reaction system can range between about 100–15,000 psi. The synthesis gas partial pressure on the average will be in the range between about 200–10,000 psi.

The process is conducted for a reaction period between about 0.5–10 hours, and typically will be in the range of about 1–5 hours.

The organic solvent employed in the process generally is a polar medium which is at least weakly alkaline with respect to the ability to form salts with strongly acidic compounds.

Illustrative of suitable basic organic solvents are methylamine, dimethylamine, trimethylamine, ethylamine, diethylamine, triethylamine, triethanolamine, tri(chloromethyl)amine, pyridine, piperidine, piperazine, and the like.

A preferred type of basic organic solvent is an aprotic organic amide. Illustrative of this type of solvent are N,N-dimethylformamide, N,N-dimethylacetamide, 1-methyl-2-pyrrolidinone, 1-methyl-2-piperidone, hexamethylphosphoric triamide, 1,1,3,3-tetramethylurea, and the like.

The basic organic solvent can be employed in admixture with other solvent media such as water, methanol, ethanol, tetrahydrofuran, diethyl ether, acetonitrile, benzonitrile, dioxane, ethylene glycol alkyl ether, ethyl acetate, butyrolactone, and the like.

Operation of the invention process appears to require a "basic" reaction medium in order to achieve a desirable rate of reaction and yield of $C_4$–$C_5$ hydroxyketone products. This requirement is satisfied by the use of a basic organic solvent.

Alternatively, the required reaction medium basicity can be provided by employing an inorganic base such as a metal hydroxide or metal carbonate, or a quaternary ammonium compound such as tetramethylammonium hydroxide, in combination with a polar solvent medium such as aqueous methanol.

The basic reaction medium environment tends to favor a "formose" type of aldol reaction mechanism with respect to the initial self-condensation of the formaldehyde molecules.

The formose reaction is described on pages 215–217 of FORMALDEHYDE, by J. Frederic Walker; Third Edition, Robert E. Krieger Publishing Company, Huntington, N.Y., 1975.

The proposed mechanism of formaldehyde aldolization involves a slow primary formation of glycolic aldehyde:

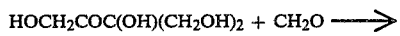

Of related interest is the disclosure of U.S. Pat. No. 2,760,983 which describes the condensation of formaldehyde to carbohydrates in an aqueous medium in the presence of a lead salt catalyst.

For purposes of the present invention process, an essential parameter for the production of $C_4$–$C_5$ hydroxyketones is the presence of a homogeneous catalyst system which contains active tungsten and Group VIII metal constituents.

As demonstrated in the Examples, the presence of tungsten metal is critical for obtaining dioxygenated $C_4$–$C_5$ hydroxyketone products. Optimal results are achieved when the tungsten metal is employed in combination with a Group VIII metal such as iron, cobalt, nickel, ruthenium, rhodium, palladium, osmium or platinum. Additional metal components may be included as promoters in the tungsten/Group VIII metal combination, e.g., metals such as titanium, zirconium, tin, and the like.

The gram-atom ratio of tungsten metal component to Group VIII metal component in the catalyst composition can be varied in the range between about 1–10:1 of tungsten to Group VIII metal.

The tungsten and Group VIII metals can be incorporated in the catalyst system in any convenient form of chemical compounds. Illustrative of suitable compounds are tungsten and Group VIII metal oxides, acetylacetonates, sulfates, tetrafluoroborates, formates, acetates, propionates, oxalates, gluconates, lactates, citrates, cyclopentadienides, and the like. Illustrative of metal compound species are tungstic acid, cobalt carbonyl, and rhodium carbonyl acetylacetonate.

The tungsten and Group VIII metal compounds initially need not be soluble in the reaction medium. Solubilization is effected or completed by contact with synthesis gas under the reaction conditions.

After the completion of a process run, the $C_4$–$C_5$ hydroxyketones and other products can be separated and recovered by conventional means such as distillation. The catalyst composition can be isolated and recycled in the process.

The following examples are further illustrative of the present invention. The components and specific ingredients are presented as being typical, and various modifications can be derived in view of the foregoing disclosure within the scope of the invention.

EXAMPLE I

This Example illustrates a process embodiment in accordance with the present invention.

A 300 cc Hastelloy C autoclave equipped with a Magnedrive mechanical stirrer is charged with 1.02 g (0.6 mmole) of $[(C_5(CH_3)_5)RhTiW_5O_{18}(C_5H_5)][(C_4H_9)_4N]^{(1)}$, 10 g (0.33 mole) of paraformaldehyde and 8.31 g (0.26 mole) of methanol in 50.5 g of 1-methyl-2-pyrrolidinone solvent.

(1)The anion is a polyoxometallate species with tetra-n-butylammonium as the cation; the organometallic ligands are pentamethylcyclopentadienyl and cyclopentadienyl.

The reactor is heated to 160° C. and maintained at 4100 psig of 1:2 ($CO:H_2$) synthesis gas. After 4–5 hours under these conditions, the autoclave is cooled to room temperature and the gas is vented.

Gas chromatographic/mass spectrometric analysis of the resulting solution indicates the yields for $C_4$–$C_5$ products to be 1.1 g of 3-hydroxy-2-butanone, 0.5 g of 2,3-butanediol and 0.65 g of 4-hydroxy-2-pentanone. Other products identified are methanol, methyl formate, dimethoxymethane and 1,1'-oxybismethoxymethane.

EXAMPLE II

A process is conducted in accordance with the procedure of Example I except that helium is employed instead of synthesis gas.

Analysis of the reaction product mixture does not indicate any presence of $C_4$–$C_5$ products. The only products formed under the reaction conditions are methanol, methyl formate, dimethoxymethane and 1,1'-oxybismethoxymethane.

EXAMPLE III

The procedure of Example I is repeated except that hydrogen alone is employed in place of synthesis gas.

The identified products are methanol, methyl formate, dimethoxymethane, and 1,1-oxybismethoxymethane. No $C_4$–$C_5$ products are formed under the reaction conditions.

When the procedure is repeated, except that carbon monoxide alone is substituted for hydrogen alone, the same type of product mixture is obtained, which additionally contains a trace quantity of 2,3-butanedione. No other $C_4$–$C_5$ products are formed under the reaction conditions.

EXAMPLE IV

The procedure of Example I is repeated, except that a 40.14 g quantity of 1-methyl-2-piperidone is utilized in place of 1-methyl-2-pyrrolidinone as the solvent.

The product mixture formed contains 0.7 g of 3-hydroxy-2-butanone, 0.25 g of 2,3-butanediol and 0.5 g of 4-hydroxy-2-pentanone. Small quantities of the Example II type of products are also present.

When the procedure of Example I is repeated, except that no 1-methyl-2-pyrrolidinone solvent is employed, the only products identified are methanol and dimethoxymethane. In the absence of a basic organic solvent, no $C_4$–$C_5$ products are formed.

EXAMPLE V

The procedure of Example I is repeated, except that methanol is not included in the reaction medium.

Analysis of the product mixture indicates the formation of 0.34 g of 3-hydroxy-2-butanone, 0.42 g of 4-hydroxy-2-pentanone and 8.9 g of methanol.

EXAMPLE VI

The Example I procedure is repeated, except that 0.54 g (0.9 mmole) of $[Rh(C_5(CH_3)_5)Cl_2]_2$ is employed as the catalyst.

Analysis of the product mixture does not indicate any $C_4$–$C_5$ product formation.

The identified products include methanol, ethanol, ethylene glycol, 1-hydroxy-2-propanone, dimethoxymethane and 1,2-propanediol.

EXAMPLE VII

The procedure of Example I is repeated, except that 1.05 g (4 mmole) of $H_2WO_4$ are employed as the catalyst.

The product mixture contains 0.43 g of 3-hydroxy-2-butanone and 0.49 g of 4-hydroxy-2-pentanone, as well as small quantities of the Example II type of formed products.

EXAMPLE VIII

The procedure of Example I is repeated, except that 0.25 g (1 mmole) of $(C_5H_5)_2TiCl_2$ is employed as the catalyst.

Analysis of the recovered product medium indicates no formation of $C_4$–$C_5$ products. Identified products include methanol, methyl formate, dimethoxymethane and 1,1'-oxybismethoxymethane.

EXAMPLE IX

This Example illustrates process embodiments in accordance with the present invention.

The procedure of Example I is repeated, except that 0.15 g (0.6 mmole) of $Rh(CO)_2(C_5H_8O_2)$[1] and 0.75 g (3 mmoles) of $H_2WO_4$ are employed as the catalyst system.
(1) The organic complexing group is acetylacetonate.

Analysis of the product mixture indicates formation of 1.0 g of 3-hydroxy-2-butanone and 0.7 g of 4-hydroxy-2-pentanone, as well as detectable quantities of the Example II type of products.

Similar results are obtained if iron, cobalt, nickel, ruthenium, palladium, osmium or platinum is substituted for rhodium in the catalyst complex with tungsten.

When the Example I procedure is repeated with the inclusion of 1.0 g (2.9 mmoles) of $Co_2(CO)_8$ as an additional catalyst component, the product yield is 0.3 g of 3-hydroxy-2-butanone, 1.13 g of 2,3-butanediol and 0.3 g of 4-hydroxy-2-pentanone. Other products include methanol, methyl acetate, acetic acid and dimethoxymethane in detectable quantities.

EXAMPLE X

The procedure of Example I is repeated, except that methanol and paraformaldehyde are not included in the reaction medium. No formation of carbon oxygenate product is evident.

When only paraformaldehyde is excluded from the reaction medium, the original methanol is the only carbon oxygenate detected in the recovered product medium.

When 7.1 g (0.15 mole) of ethanol are employed in place of methanol in the Example I procedure, there is obtained 1.3 g of 3-hydroxy-2-butanone and 0.97 g of 4-hydroxy-2-pentanone, and a quantity of methanol formed by reduction of the formaldehyde starting material.

What is claimed is:

1. A process for the conversion of formaldehyde to higher oxygenated hydrocarbons which comprises reacting formaldehyde, carbon monoxide and hydrogen in a basic organic solvent medium in the presence of a soluble catalyst composition consisting essentially of tungsten and Group VIII metal components, to yield a product mixture comprising $C_4$–$C_5$ hydroxyketones.

2. A process in accordance with claim 1 wherein the reaction is conducted at a temperature between 75°–250° C. and a pressure between about 1000–15,000 psi for a reaction period between about 0.5–10 hours.

3. A process in accordance with claim 1 wherein the carbon monoxide and hydrogen are employed in a molar ratio between 1:2–2:1 of carbon monoxide to hydrogen.

4. A process in accordance with claim 1 wherein the basic organic solvent medium comprises an organic amine or amide.

5. A process in accordance with claim 1 wherein the catalyst composition contains tungsten and rhodium metal components.

6. A process in accordance with claim 1 wherein the catalyst composition contains tungsten and cobalt metal components.

7. A process in accordance with claim 1 wherein the catalyst composition contains tungsten, rhodium and titanium metal components.

8. A process for the production of hydroxyketones which comprises reacting formaldehyde, carbon monoxide and hydrogen in an aprotic organic amide solvent medium in the presence of a soluble catalyst composition consisting essentially of tungsten and Group VIII metal compounds, at a temperature between about 100°–200° C. and a pressure between about 2000–10,000 psi to yield a product mixture comprising 3-hydroxy-2-butanone and 4-hydroxy-2-pentanone.

9. A process in accordance with claim 8 wherein the solvent medium is 1-methyl-2-pyrrolidinone.

10. A process in accordance with claim 8 wherein the solvent medium is 1-methyl-2-piperidone.

11. A process in accordance with claim 8 wherein the catalyst composition contains tungsten and rhodium metal components.

12. A process in accordance with claim 8 wherein the catalyst composition contains tungsten and cobalt metal components.

13. A process in accordance with claim 8 wherein the catalyst composition contains tungsten, rhodium and titanium components.

14. A process in accordance with claim 8 wherein the catalyst composition is a salt of a tungsten and rhodium metal-containing anion and a quaternary ammonium cation.

15. A process in accordance with claim 8 wherein the product mixture contains 2,3-butanediol.

16. A process in accordance with claim 1 wherein the catalyst composition includes a promoter component.

17. A process in accordance with claim 8 wherein the catalyst composition includes a promoter component.

* * * * *